US00PP30030P3

(12) United States Plant Patent
Jacobs

(10) Patent No.: US PP30,030 P3
(45) Date of Patent: Dec. 25, 2018

(54) ***CHRYSANTHEMUM* PLANT NAMED 'ZANMUBONITA YELLOW'**

(50) Latin Name: ***Chrysanthemum* x *morifolium* Ramat.**
Varietal Denomination: Zanmubonita Yellow

(71) Applicant: Van Zanten Breeding BV, Valkenburg (NL)

(72) Inventor: Henricus Cornelius Maria Jacobs, Valkenburg (NL)

(73) Assignee: VAN ZANTEN BREEDING BV, Valkenburg (NL)

( * ) Notice: Subject to any disclaimer, the term of this patent is extended or adjusted under 35 U.S.C. 154(b) by 31 days.

(21) Appl. No.: 15/530,245

(22) Filed: Dec. 16, 2016

(65) Prior Publication Data

US 2018/0177094 P1 Jun. 21, 2018

(51) Int. Cl.
*A01H 5/02* (2018.01)
*A01H 6/14* (2018.01)

(52) U.S. Cl.
USPC ..... Plt./295
CPC ..... *A01H 6/1424* (2018.05); *A01H 5/02* (2013.01)

(58) Field of Classification Search
USPC ..... Plt./295
See application file for complete search history.

*Primary Examiner* — Keith O. Robinson
(74) *Attorney, Agent, or Firm* — Steptoe & Johnson LLP

(57) ABSTRACT

A new and distinct *chrysanthemum* plant named 'Zanmubonita Yellow' is disclosed, it is characterized by its medium sized, double type blooms with yellow color ray florets and response time of 7 weeks. The new plant is normally used for commercial cut flower production.

3 Drawing Sheets

Botanical designation: *Chrysanthemum* x *morifolium* Ramat.
Cultivar denomination: 'Zanmubonita Yellow'.

RELATED CULTIVARS

'Zanmubonita Yellow' is a mutant plant of 'Zanmubonita' (unpatented).

BACKGROUND OF THE INVENTION

The present invention comprises a new and distinct cultivar of *chrysanthemum*, botanically known as *Chrysanthemum* x *morifolium*, and referred to by the denomination 'Zanmubonita Yellow'; the description is based on plants of about 10 weeks old.

'Zanmubonita Yellow' is a product of a breeding and selection program to produce new *chrysanthemum* cultivars for cut flower commercial applications. The new plant cultivar is a naturally whole plant mutant of a parent *chrysanthemum* named 'Zanmubonita' (unpatented).

A comparison with the parent is made in the section 'DESCRIPTION OF THE INVENTION' below. The new cultivar was discovered as a whole plant mutation in June 2014 by Henricus Cornellius Maria Jacobs in a controlled environment (greenhouse) in Valkenburg Z-H, The Netherlands. The first act of asexual reproduction of 'Zanmubonita Yellow' was accomplished when vegetative cuttings were taken from the initial selection and propagated further in Valkenburg Z-H, The Netherlands.

SUMMARY OF THE INVENTION

The present invention is a new and distinct variety of a cut type *chrysanthemum* bearing medium sized double type blooms with yellow ray-florets and a response time of seven weeks.

BRIEF DESCRIPTION OF THE DRAWINGS

The present invention of a new and distinct variety of *chrysanthemum* (of about 10 weeks) is shown in the accompanying drawings, the color being as nearly true as possible with color photographs of this type.

DESCRIPTION OF THE INVENTION

Figure 1:
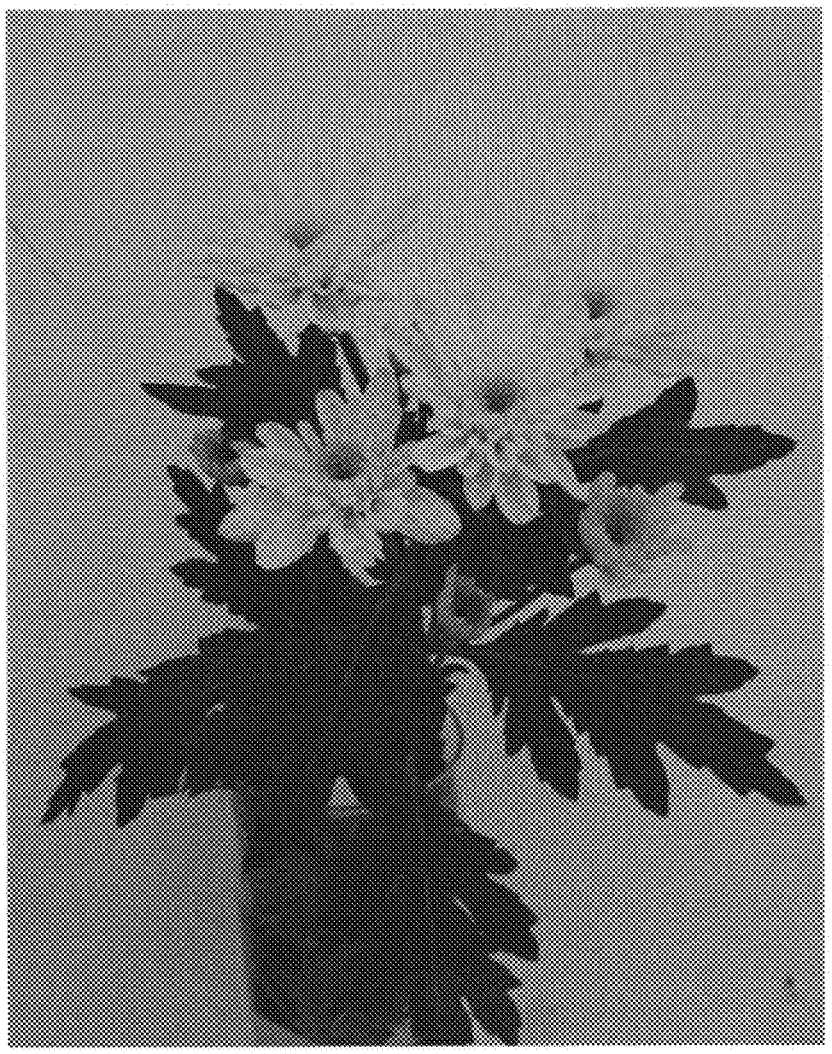
FIG. 1 shows a plant of the cultivar in full bloom.
Figure 2:
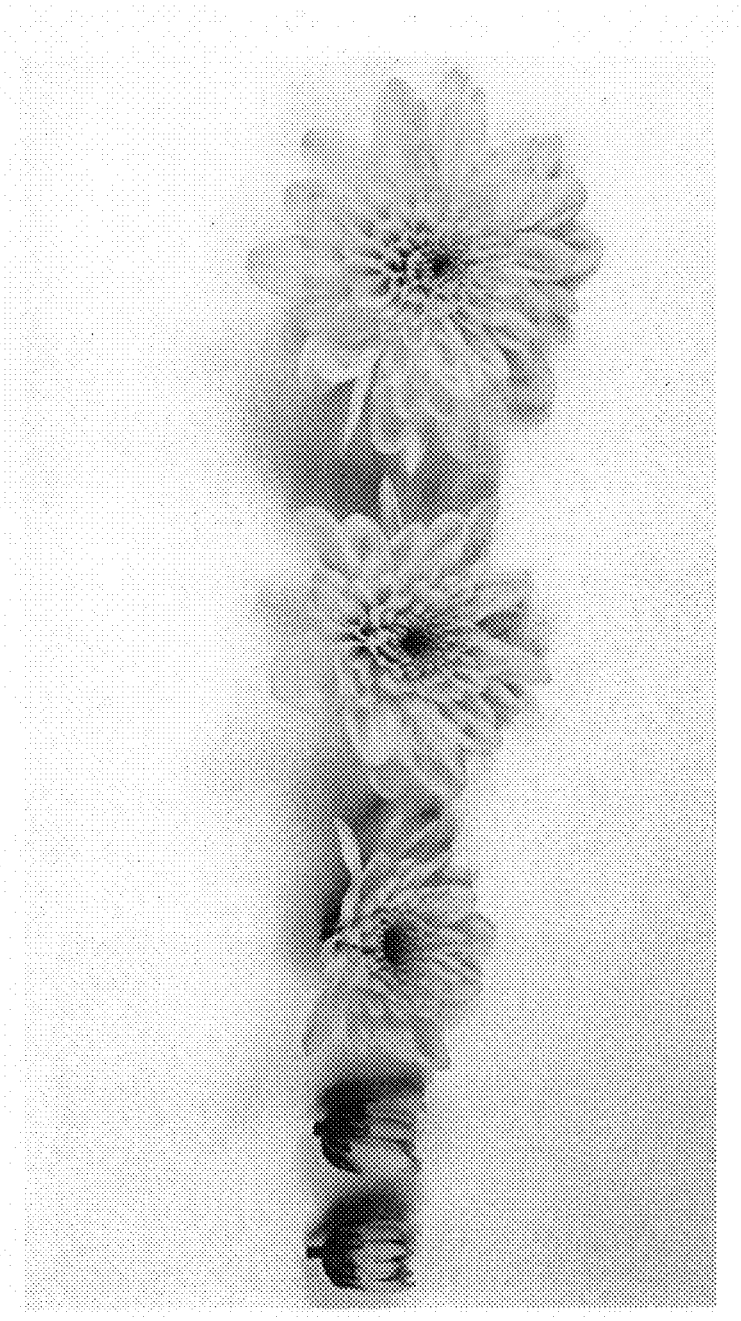
FIG. 2 shows the various stages of bloom of the new cultivar.
Figure 3:
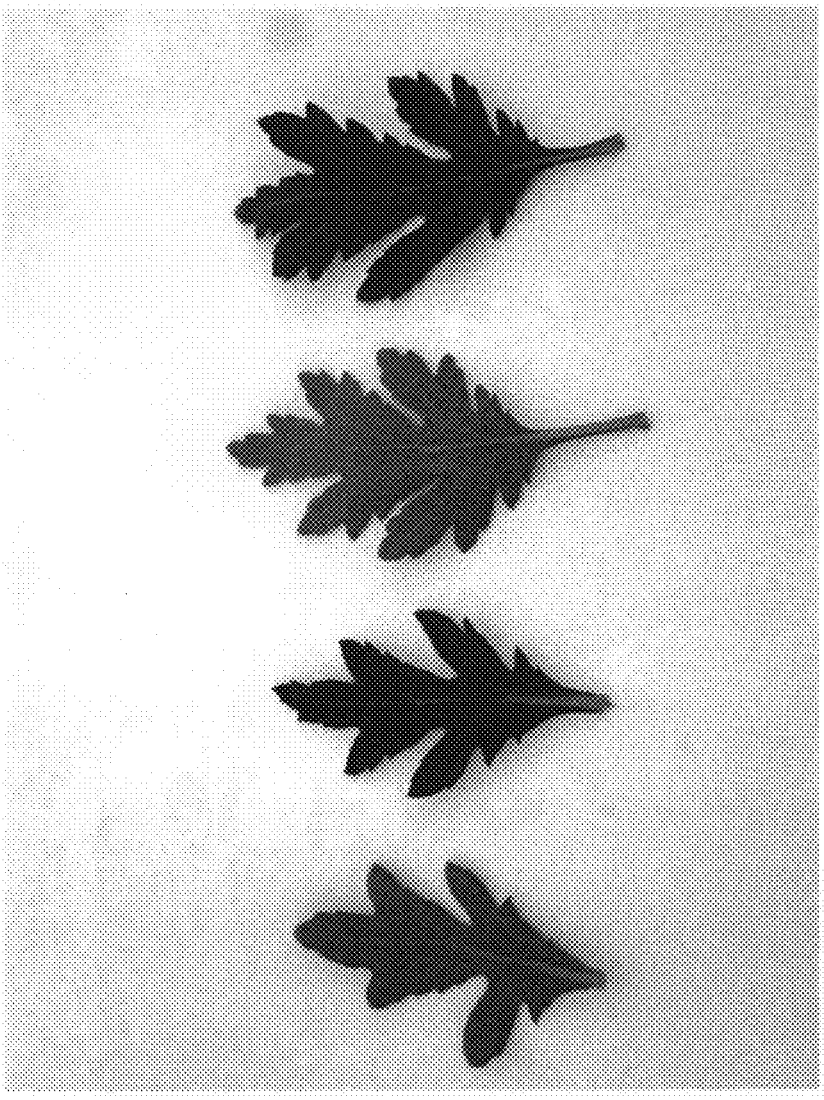
FIG. 3 shows the foliage of the new cultivar.

The observations and measurements were gathered from plants grown in August to September 2016 in a greenhouse in Valkenburg Z-H, the Netherlands in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 49 days. After the long day period to flowering growth retardants (Alar) were applied 2 to 3 times in an average dose of 2.5 gram/liter water. No tests were done on disease or insect resistance or susceptibility. No tests were done on cold or drought resistance. This new variety of *chrysanthemum* has been found to retain its distinctive characteristics throughout successive propagations however the phenotype may vary significantly with variations in environment such as light intensity and temperature.

From the cultivars known to inventor the most similar existing cultivar in comparison to 'Zanmubonita Yellow' is 'Zanmubonita'. When 'Zanmubonita' and 'Zanmubonita Yellow' are being compared the following differences and similarities are noticed: The difference of 'Zanmubonita' and 'Zanmubonita Yellow' is ray floret color. For that characteristic 'Zanmubonita Yellow' has been selected out of 'Zanmubonita'; ray florets of 'Zanmubonita Yellow' are yellow, while those of 'Zanmubonita' are white. All other characteristics of 'Zanmubonita' and 'Zanmubonita Yellow' are similar. A second similar variety is 'Sunny Eurobelle' (unpatented), which differs in inflorescence size with 'Zanmubonita Yellow'. Inflorescences of 'Sunny Eurobelle' are smaller in size than those of 'Zanmumbonita Yellow'.

The following is a description of the plant and characteristics that distinguish 'Zanmubonita Yellow' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* × *morifolium* Ramat. 'Zanmubonita Yellow'

| | |
|---|---|
| **Bud** | |
| Size: | Medium; cross-section 8 mm, height 7 mm |
| Shape: | Round |
| Texture: | Pubescent |
| Outside color: | Greyed-green 191A |
| **Phyllaries** | |
| Number: | 24, arranged in 3 rows |
| Shape: | Elliptic |
| Apex: | Acute |
| Base: | Truncate |
| Margin: | Entire |
| Color: | Upper side: Green 136A |
| Under side: | Green 137A |
| Length and width: | 10 mm; 3.5 mm |
| Texture: | Pubescent (upper side) |
| **Inflorescences** | |
| Spray Form: | Cylindrical |
| Inflorescence Type: | Double |
| Inflorescence Height: | 2 cm |
| Inflorescence Diameter: | 7-8 cm |
| Peduncle length: | 10-17 cm |
| Peduncle color: | Green 138A |
| Peduncle diameter: | 2 mm |
| Peduncle texture: | Pubescent |
| Number per branch: | Approx. 16-17 inflorescences |
| Seeds: | Not observed. |
| Fragrance: | Faint chrysanthemum odor |
| **Color inflorescences** | |
| Center of inflorescence: | Immature stage: Yellow-green 143C; Mature stage: Yellow-green 144C |
| Color of upper side of ray florets: | Yellow 5C |
| Color of lower side of ray florets: | Yellow 5C |
| Tonality from distance: | A cut mum with yellow blooms and a green center |
| Color of ray florets after aging of the plant: | Yellow 5C |
| **Ray florets** | |
| Number of types: | One |
| Type: | Ligulate |
| Texture: | Upper and under side smooth |
| Number: | 100-110 |
| Shape: | Elliptic |
| Apex: | Rounded |
| Base: | Acute |

TABLE 1-continued

Botanical Description of *Chrysanthemum* × *morifolium* Ramat. 'Zanmubonita Yellow'

| | |
|---|---|
| Cross-section: | Weakly concave |
| Longitudinal axis: | Straight |
| Diameter of corolla tube: | 1 mm |
| Length of corolla tube: | 2 mm |
| Ray floret margin: | Entire |
| Ray floret length: | 1.8-4 cm |
| Ray floret width (outer row): | 4-12 mm |
| Ratio length/width: | Medium |
| **Disc florets** | |
| Disc diameter: | 1 mm |
| Distribution of disc florets: | Very few, only visible in mature stage of inflorescence |
| Shape: | Tubular |
| Color: | Yellow-green 145C at base to Green Yellow 143C at apex |
| Length: | 4 mm |
| Diameter: | 0.5 mm |
| **Receptacle** | |
| Color: | Yellow-green 145D |
| Shape: | Domed raised |
| Height: | 5 mm |
| Diameter: | 6 mm |
| **Reproductive Organs** | |
| Androecium: | Present on only disc florets |
| Stamen length: | 3 mm |
| Stamen color: | Yellow-green 144A |
| Anther color: | Yellow 2A |
| Pollen: | Not observed |
| Gynoecium: | Present on both ray and disc florets |
| Style color: | Yellow-green 154C |
| Style length: | 4 mm |
| Stigma color: | Yellow 7A |
| Stigma width: | 1 mm |
| Ovary: | Enclosed in calyx |
| Ovary color: | Yellow-green 149D |
| **Plant** | |
| Plant type: | Non-bushy |
| Growth habit: | Upright |
| Growth rate: | Medium |
| Height: | 105-115 cm |
| Width: | 25 cm |
| Stem strength: | Strong |
| Stem color: | Green 138B |
| Stem texture: | Smooth, slightly pubescent |
| Stem diameter: | 6-7 mm |
| Stem anthocyanin coloration: | absent |
| Internode length: | 1.8-2 cm |
| Response time: | 49 days |
| Roots: | Short, fibrous |
| Root color: | White 155A |
| **Foliage** | |
| Glossiness: | Weakly (upper side) |
| Leaf color: | Upper side: Green 136A; Under side: Green 137C |
| Color midvein: | Upper side: Yellow-green 147D; Under side: Yellow-green 148D |
| Size: | Medium; length 10-12 cm, width 4.5-6.5 cm |
| Quantity per stem: | 26-30 |
| Shape: | Elliptic |
| Texture upper side: | Sparsely pubescent |
| Texture under side: | Pubescent |
| Venation arrangement: | Pinnate |
| Shape of margin: | Serrated |
| Shape of base of sinus between lateral lobes: | Rounded |
| Margin of sinus between lateral lobes: | Diverging |

TABLE 1-continued

| Botanical Description of *Chrysanthemum* × *morifolium* Ramat. 'Zanmubonita Yellow' | |
|---|---|
| Shape of base: | Attenuate to Truncate |
| Apex: | Pointed |
| Petiole length: | 2 cm |
| Petiole diameter: | 2.5-3 mm |
| Petiole attitude: | Moderately upwards |
| Petiole color: | Yellow-green 147D |
| Petiole strength: | Medium |
| Stipules: | 1 to 1.5 cm |

TABLE 2

Differences of the new plant with the comparison varieties.

| | 'Zanmubonita Yellow' | 'Zanmubonita' | 'Sunny Eurobelle' |
|---|---|---|---|
| Color ray florets | Yellow 5C | White 155D | Yellow 5B |
| Inflorescence size | 7-8 cm | 7 cm | 6-6.5 cm |

I claim:

1. A new and distinct *chrysanthemum* plant named 'Zanmubonita Yellow' as described and illustrated.

* * * * *